(12) United States Patent
Leu et al.

(10) Patent No.: US 8,067,163 B2
(45) Date of Patent: Nov. 29, 2011

(54) DETERMINATION OF THE BIOLOGICAL FUNCTION OF A TARGET GENE IN A CELL

(75) Inventors: Yu-Wei Leu, Chang Hua (TW); Shu-Huei Hsiao, Chang Hua (TW); Tim Hui-Ming Huang, Columbus, OH (US)

(73) Assignee: National Chung Cheng University, Ming-Hsiung, Chia-Yi (TW)

( * ) Notice: Subject to any disclaimer, the term of this patent is extended or adjusted under 35 U.S.C. 154(b) by 226 days.

(21) Appl. No.: 12/135,540

(22) Filed: Jun. 9, 2008

(65) Prior Publication Data

US 2009/0305250 A1    Dec. 10, 2009

(51) Int. Cl.
*C12Q 1/68* (2006.01)
(52) U.S. Cl. .......................................................... 435/6
(58) Field of Classification Search ................... 435/6
See application file for complete search history.

(56) References Cited

U.S. PATENT DOCUMENTS

| | | | |
|---|---|---|---|
| 5,840,497 A | 11/1998 | Holliday | |
| 6,355,239 B1* | 3/2002 | Bruder et al. | 424/93.1 |
| 6,573,099 B2* | 6/2003 | Graham | 435/455 |
| 2004/0006036 A1* | 1/2004 | Hu et al. | 514/44 |
| 2005/0196769 A1* | 9/2005 | Fan et al. | 435/6 |
| 2005/0287668 A1* | 12/2005 | Finney | 435/455 |
| 2009/0275032 A1* | 11/2009 | Eilertsen et al. | 435/6 |

FOREIGN PATENT DOCUMENTS

WO    WO 99/24560    5/1999

OTHER PUBLICATIONS

Aspenström, Pontus "A Cdc42 Target Protein with Homology to the Non-Kinase Domain of FER has a Potential Role in Regulating the Actin Cytoskeleton," *Current Biology*, 7:479-487 (1997).
Cappello et al., "The Rho-GTPase cdc42 Regulates Neural Progenitor Fate as the Apical Surface," *Nature Neuroscience*, 9(9): 1099-1107 (2006).
Lee et al., "In Vitro Hepatic Differentiation of Human Mesenchymal Stem Cells," *Hepatology*, 40:1275-1284 (2004).
Leu et al., "Loss of Estrogen Receptor Signaling Triggers Epigenetic Silencing of Downstream Targets in Breast Cancer," *Cancer Research*, 64:8184-8192 (2004).
Yan et al., "Mapping Geographic Zones of Cancer Risk With Epigenetic Biomarkers in Normal Breast Tissue," *Clin. Cancer Res.*, 12(22):6626-6636 (2006).
Holbert et al., "Cde42-Interacting Protein 4 Binds to Huntingtin: Neuropathologic and Biological Evidence for a Role in Huntinton's Disease," *PNAS*, vol. 100, No. 5, :2712-2717, Mar. 4, 2003.

* cited by examiner

*Primary Examiner* — Brian Whiteman
(74) *Attorney, Agent, or Firm* — Occhiuti Rohlicek & Tsao LLP (57) ABSTRACT

Disclosed herein is a method to determine the biological function(s) of a target gene in a cell, the steps of which involve separately culturing a first population and a second population of the cell under same culturing conditions, the first population of the cell differing from the second population of the cell in that the first population of the cell has accepted the introduction of a methylated polynucleotide; comparing the first population and the second population of the cell to determine which biological difference(s) is/are present therebetween; and determining which biological function(s) the target gene is associated with based on the determined biological difference(s) between the first population and the second population of the cell.

7 Claims, 6 Drawing Sheets

DETERMINATION OF THE BIOLOGICAL FUNCTION OF A TARGET GENE IN A CELL

BACKGROUND OF THE INVENTION

1. Field of the Invention

This invention relates to a method to determine the biological function of a target gene in a cell, which comprises: separately culturing a first population and a second population of the cell under same culturing conditions, the first population of the cell differing from the second population of the cell in that the first population of the cell has accepted the introduction of a methylated polynucleotide; comparing the first population and the second population of the cell to determine which biological difference(s) is/are present therebetween; and determining which biological function(s) the target gene is/are associated with based on the determined biological difference(s) between the first population and the second population of the cell.

2. Description of the Related Art

As genomes of numerous species have been sequenced completely, gene function research has drawn attention of scientists. To date, studies aimed at the biological function of a given gene mostly rely on traditional genetic and molecular manipulations such as knock-out, knock-in mutagenesis/transgenic assays, as well as knock down studies using small interfering RNA (siRNA) and antisense RNAs. Amongst these studies, the application of siRNA where the siRNA interferes with the expression of a specific gene has proved to be one of the most powerful means for interrogation of the gene's functions and can be used to target a specific gene or a batch of genes. However, the cost of siRNA is high and siRNA is unstable during delivery. Besides, these studies are all difficult to be expanded from the results of genomic profiling to a high-throughput interrogation of the functions of genes, indicating that their constructions/designs are more time-consuming.

Therefore, there still remains a need in the art to develop a method for functional analysis of specific gene(s) that is less expensive and more stable and convenient in practical use.

In addition to siRNAs, methylated oligonucleotides have been synthesized and used to inhibit the expression of genes as well. For example, U.S. Pat. No. 5,840,497 discloses a method for the silencing of specific genes by DNA methylation. The method involves introducing into a cell a single-stranded oligonucleotide containing 5-methyl deoxycytosine, wherein the single-stranded oligonucleotide has a sequence complementary to a sequence within the promoter region of the gene to be silenced, and wherein the sequence within the promoter region contains at least one CpG doublet.

WO 99/24560 discloses a method of inhibiting the expression of a gene in a cell, comprising the step of administering to the cell a single-stranded oligonucleotide comprising nucleotide units wherein at least one cytosine of a cytosine-guanine base pair contains a methyl group at the 5 position of the cytosine nucleotide.

In this invention, the applicants attempted to develop a method to determine the biological function(s) of a target gene in a cell using a methylated polynucleotide, the sequence of which is identical to or fully complementary to that of a portion of the target gene's nucleotide sequence at the promoter and/or the first exon region thereof. According to the applicants' method, a first population of the cell accepting transfection with the methylated polynucleotide is compared with a second population of the cell without accepting the transfection treatment. The observed biological difference(s) between the first and second populations of the cell is/are then relied upon as a basis for determining the biological function(s) of the target gene in the cell. To prove the practicality and usage of the applicant's method, a gene encoding thyroid hormone receptor interacting protein 10 (TRIP10) was chosen as the target gene and a methylated Trip10 DNA directed to the Trip10 promoter was tested in experiments using either human or rat mesenchymal stem cells (MSCs).

There has been an early report indicating that thyroid hormone receptor interacting protein 10 (TRIP10), also known as Cdc42-interacting protein 4 (CIP4), binds to activated Cdc42 in vitro and in vivo, suggesting that TRIP10 may act as a link between Cdc42 signaling and regulation of the actin cytoskeleton (P. Aspenström (1997), *Curr. Biol.*, 7:479-487). Cdc42 plays a role in cell-cycle control, as it is needed for progression through G1. Recent evidence indicates that Cdc42 has a role in neural progenitors, maintaining them in a self-renewing state, a prerequisite for the maintenance of stem cells into adulthood (S. Cappello et al. (2006), *Nature Neuroscience*, 9:1099-1107). Thus, TRIP10 association with Cdc42 implies that TRIP10 may be involved in cell-cycle/growth.

It has also been reported that CIP4 accumulation and toxicity in striatal neurons may play a role in Huntington's disease (HD) pathogenesis (S. Holbert et al. (2003), *PNAS*, 100:2712-2717). Clinical evidence also suggests the interaction of TRIP10 with huntingtin (htt), the protein that regulates both cell growth and apoptosis and its abnormality is identified in the pedigree studies of Huntington's disease (S. Holbert et al. (2003), *PNAS*, 100:2712-2717). These findings indicate that TRIP10 may be involved in cell growth and apoptosis due to the interaction between TRIP10 and htt. However, the role of the Trip10 gene in cell fate/induction remains largely unknown.

The experimental results obtained by the applicants' method reveal that suppressed Trip10 expression is a critical signal for MSC-to-neuron differentiation and preventing MSCs from death. It is thus believed that the method developed by the applicants is an efficient and powerful tool for analyzing the biological functions of genes.

SUMMARY OF THE INVENTION

Therefore, this invention provides a method to determine which biological function a target gene in a cell is associated with, the target gene having a nucleotide sequence including a promoter and a first exon region, the method comprising:

separately culturing a first population and a second population of the cell under same culturing conditions, the first population of the cell differing from the second population of the cell in that the first population of the cell has accepted the introduction of a methylated polynucleotide selected from the group consisting of:
  (i) a single-stranded DNA molecule, which has a nucleotide sequence identical to or fully complementary to that of a portion of the target gene's nucleotide sequence at the promoter and/or the first exon region thereof;
  (ii) a double-stranded DNA molecule, one strand of which has a nucleotide sequence identical to or fully complementary to that of a portion of the target gene's nucleotide sequence at the promoter and/or the first exon region thereof; and
  (iii) a combination of (i) and (ii);

comparing the first population and the second population of the cell to determine which biological difference is present therebetween; and determining which biological function the target gene is associated with based on the determined biological difference present between the first population and the second population of the cell.

It is contemplated that the practice of this invention is not limited to specific cells. In fact, this invention can be applied to a diversity of prokaryotic and eukaryotic cells, including bacterial cells, fungal cells, plant cells, insect cells and mammalian cells, and is available for use in industry and in agriculture, pharmaceutical industry, food industry, etc.

BRIEF DESCRIPTION OF THE DRAWINGS

The above and other features and advantages of the present invention will become apparent in the following detailed description of the preferred embodiment with reference to the accompanying drawing, of which:

FIG. 8 shows the TRIP10 distribution in rat MSCs transfected with me_Trip10 DNA versus mock-transfected rat MSCs with or without cultivation with neuronal induction medium for 24 hours, in which the nuclei (blue colored) of the cells were localized by staining with DAPI, and the presence of TRIP10 in the cells was observed by incubating the cells with an anti-TRIP10 antibody (AbCam, #33874), followed by incubation with a secondary antibody conjugated with Fluorescein (Vector Lab, Fl-1000). The top three panels marked with the symbol "−" represent mock-transfected rat MSCs before neuronal induction treatment, the middle three panels marked with the symbol "+" represent mock-transfected rat MSCs after neuronal induction treatment, and the bottom three panels represent rat MSCs transfected with me_Trip10 DNA before neuronal induction treatment.

DETAILED DESCRIPTION OF THE INVENTION

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless otherwise defined, all technical and scientific terms used herein have the meaning commonly understood by a person skilled in the art to which this invention belongs. One skilled in the art will recognize many methods and materials similar or equivalent to those described herein, which could be used in the practice of this invention. Indeed, this invention is in no way limited to the methods and materials described. For clarity, the following definitions are used herein.

The term "gene" as used herein refers to a DNA sequence, including but not limited to a DNA sequence that can be transcribed into mRNA which can be translated into polypeptide chains, transcribed into rRNA or tRNA or serve as recognition sites for enzymes and other proteins involved in DNA replication, transcription and regulation. This definition includes various sequence polymorphisms, mutations, and/or sequence variants wherein such alterations do not affect the function of the gene product. The term "gene" is intended to include not only regions encoding gene products but also regulatory regions including, e.g., promoters, termination regions, translational regulatory sequences (such as ribosome binding sites and internal ribosome entry sites), enhancers, silencers, insulators, boundary elements, replication origins, matrix attachment sites, and locus control regions. The term "gene" further includes all introns and other DNA sequences spliced from the mRNA transcript, along with variants resulting from alternative splice sites. The term "gene" includes, but is not limited to, structural genes, immunity genes and secretory (transport) genes.

The term "target gene" as used herein refers to a specific gene whose biological function in a cell is the subject to be analyzed. The target gene may be derived from any living or once living prokaryotic or eukaryotic cells, including bacterial cells, fungal cells, plant cells, insect cells and mammalian cells.

The term "promoter" as used herein refers to a DNA regulatory region capable of binding RNA polymerase in a cell and initiating transcription of a downstream (3' direction) coding sequence. The promoter is bound at its 3' terminus by the translation start codon of a coding sequence and extends upstream (5' direction) to include a minimum number of bases or elements necessary to initiate transcription.

The term "exon" as used herein refers to a region of a gene whose nucleotide sequence is transcribed by RNA polymerase and is present in both the primary heteronuclear RNA transcript and the mature messenger RNA. Exons are intermingled with introns, which are non-coding sequences in the DNA and are subsequently eliminated by splicing when the DNA is transcribed into mRNA. Exons are numbered according to the nucleotide position starting from the A in the initiation codon "ATG." An exon may encode part of or all of an expressed protein.

The term "first exon" as used herein refers to the first region of a gene that encodes a polypeptide or a polypeptide region and is located downstream of the promoter region of the gene.

As used herein, the term "upstream" and "downstream" refer to the position of an element of nucleotide sequence. "Upstream" signifies an element that is more 5' than the reference element. "Downstream" signifies an element that is more 3' than the reference element.

The term "polynucleotide" as used herein refers to a sequence of nucleotides connected by phosphodiester linkages. A polynucleotide of this invention can be a deoxyribonucleic acid (DNA) molecule or ribonucleic acid (RNA) molecule in either single- or double-stranded form. Nucleotide bases are indicated herein by a single letter code: adenine (A), guanine (G), thymine (T), cytosine (C), inosine (I) and uracil (U). A polynucleotide of this invention can be prepared using standard techniques well known to one of ordinary skill in the art. This term is not to be construed as limiting with respect to the length of a polymer, and encompasses known analogues of natural nucleotides, as well as nucleotides that are modified in the sugar and/or phosphate moieties. This term also encompasses nucleic acids containing modified backbone residues or linkages, which are synthetic, naturally occurring, and non-naturally occurring, which have similar binding properties as the reference nucleic acid, and which are metabolized in a manner similar to the reference nucleotides.

The term "identical to" as used herein refers to two or more nucleotide sequences that are the same when compared and aligned for maximum correspondence, as measured using sequence comparison algorithms or by inspection.

As used herein, the term "complementary to" refers to the ability of two nucleotide sequences to bind sequence-specifically to each other by hydrogen bonding through their purine and/or pyrimidine bases according to the usual Watson-Crick rules for forming duplex nucleic acid complexes.

The term "transfection" as used herein refers to the introduction of an exogenous nucleic acid molecule into a selected host cell. According to techniques known in the art, an exogenous nucleic acid molecule (e.g., a recombinant DNA construct or a recombinant vector) can be introduced into a competent host cell by various techniques, such as gene gun, electroporation, microinjection, heat shock, calcium phosphate precipitation, magnetofection, nucleofection, lipofection, use of transfection reagents, use of cationic polymers, etc.

In this invention, the applicants provide a method to determine which biological function a target gene in a cell is associated with, the target gene having a nucleotide sequence including a promoter and a first exon region, the method comprising:
separately culturing a first population and a second population of the cell under same culturing conditions, the first population of the cell differing from the second population of the cell in that the first population of the cell has accepted the introduction of a methylated polynucleotide selected from the group consisting of:
(i) a single-stranded DNA molecule, which has a nucleotide sequence identical to or fully complementary to that of a portion of the target gene's nucleotide sequence at the promoter and/or the first exon region thereof;
(ii) a double-stranded DNA molecule, one strand of which has a nucleotide sequence identical to or fully complementary to that of a portion of the target gene's nucleotide sequence at the promoter and/or the first exon region thereof; and
(iii) a combination of (i) and (ii);
comparing the first population and the second population of the cell to determine which biological difference is present therebetween; and
determining which biological function the target gene is associated with based on the determined biological difference between the first population and the second population of the cell.

In a preferred embodiment of this invention, the methylated polynucleotide is a double-stranded DNA molecule, one strand of which has a nucleotide sequence identical to that of a portion of the target gene's nucleotide sequence at the promoter thereof.

In another preferred embodiment of this invention, the methylated polynucleotide is a single-stranded DNA molecule, which has a nucleotide sequence identical to that of a portion of the target gene's nucleotide sequence at the promoter thereof.

According to this invention, the methylated polynucleotide has at least one methylated cytosine nucleotide. The methylated polynucleotide may be methylated at the fifth carbon position of the cytosine nucleotide by the action of DNA methyltransferase or be synthesized chemically or enzymatically. In a preferred embodiment of this invention, the methylated polynucleotide is a PCR-generated fragment using methylated cytosine nucleotide as starting material.

According to this invention, the methylated polynucleotide may have a length ranging from 22 to 2,000 nucleotides or even longer. Preferably, the methylated polynucleotide has a length ranging from 60 to 1,500 nucleotides. More preferably, the methylated polynucleotide has a length ranging from 150 to 1000 nucleotides. In a preferred embodiment of this invention, the methylated polynucleotide has a length of 500 nucleotides.

According to this invention, the methylated polynucleotide, independent of being designed based on the nucleotide sequence of the promoter or the first exon region of the target gene, will spontaneously induce a high degree of methylation of the target gene when introduced into the cell, leading to the change of the cell in terms of morphological, or biochemical or physiological state.

According to this invention, the biological difference may be selected from the group consisting of a biochemical difference, a physiological difference, a morphological difference, and combinations thereof. Examples of the biological difference include, but are not limited to: a promotion or inhibition of the production of an enzyme, extracellular matrix, adhesion molecule, transcription controlling factor, growth factor, hormone, cytokine, differentiation/induction factor, chemotaxic factor, and neurotransmitter; production of a growth factor, hormone, cytokine, chemotaxic factor capable of promoting the migration of leukocyte, protein capable of increasing the phagocytosis or bacteriocidal ability of a leukocyte, lymphocyte growth factor, T cell activating factor, T cell growth factor, antigen-specific inhibiting factor specifically acting on an immune system, and antigen-nonspecific inhibiting factor; liberation of arachidonic acid, liberation of acetylcholine, liberation of $Ca^{+2}$, generation of cAMP, generation of cGMP, production of inositol phosphate metabolites, change in cell membrane potential, phosphorylation of a protein, activating of c-fos, and change in pH; and elongation of neutrite, shrinking or expansion of the cell, and generation or disappearance of intracellular granules.

It is contemplated that the method of this invention can also be applied in analyzing a batch of genes, which cooperate with each other so as to exhibit specific biological function(s) in the cell.

The present invention will be described in more detail with reference to the following examples, which are given solely for the purpose of illustration only and are not intended to limit the scope of the present invention.

EXAMPLES

Experimental Materials

1. Human Mesenchymal Stem Cells (MSCs):

The human MSCs were kindly provided by Dr. Kuan-Der Lee (Chang-Gung Memorial Hospital, Chia-Yi, Taiwan). Protocols for the isolation and culture of human MSCs are described in K. D. Lee et al. (2004), *Hepatology*, 40(6):1275-1284. In brief, human bone marrow was aspirated from the iliac crest of healthy donors. All samples were collected with informed consent. Mononuclear cells were obtained by negative immunodepletion of CD3, CD14, CD19, CD38, CD66b and glycophorin-A positive cells using RosetteSep® (StemCell Technologies, Vancouver, BC, Canada) according to the manufacturer's instructions, followed by Ficoll-Paque (Amersham-Pharmacia, Piscataway, N.J.) density-gradient centrifugation (1.077 g/cm$^3$), and then plated into tissue culture flasks (Becton Dickinson, Franklin Lakes, N.J.) containing expansion medium. The expansion medium has composed of Iscove's modified Dulbecco's medium (IMDM, Gibco BRL, Grand Island, N.Y.) supplemented with 10% fetal bovine serum (FBS)(Hyclone, Logan, Utah), 10 ng/mL epidermal growth factor (EGF), 10 ng/mL basic fibroblast growth factor (bFGF), 100 mg/mL penicillin/streptomycin, and 2 mM L-glutamine (Gibco BRL). Cells were allowed to adhere overnight in an incubator with culture conditions set at 37° C. and 95% $O_2$/5% $CO_2$, and non-adherent cells were washed out with medium changes. Medium changes were performed twice a week.

Cell passages were performed when the cell density reached 90% confluence. During passage, the culture medium was removed, and the cells were washed twice with PBS, followed by the addition of 1% trypsin-EDTA so as to detach the cells from the bottom of the tissue culture flask. Thereafter, fresh expansion medium was added to neutralize trypsin's activity, and the medium was repeatedly pipetted using a pipette so as to disperse the detached cells contained therein. The cell suspension thus formed was transferred into a centrifuge tube and centrifuged at 600 rpm for 5 minutes. After removal of supernatant, fresh expansion medium was added into the centrifuge tube to re-suspend the cell pellet. The resultant cell suspension was dispensed into petri dishes and cultivated in an incubator with culture conditions set at 37° C. and 95% $O_2$/5% $CO_2$.

2. Rat Mesenchymal Stem Cells:

The rat MSCs were washed off from the bone marrow dissected out from rat hind leg with 1×PBS. The wash-offs were plated into a 75T flask containing alpha-minimum essential medium (α-MEM) supplemented with 20% newborn calf serum, 2 mM L-glutamine and 10 mg/mL penicillin/streptomycin, followed by incubation in an incubator with culture conditions set at 37° C. and 95% $O_2$/5% $CO_2$ for 4 days. Thereafter, the medium and non-adherent cells were aspirated and fresh medium was added. The adherent cells were checked with CD133 expression by immunostaining. Cell passages were performed in the same way as described above for human MSCs.

Experimental Procedures:

1. Cloning of the Trip10 Promoter:

Based on the nucleotide sequence deposited in the NCBInr database under NCBI accession number NM_004240 [*Homo sapien* thyroid hormone receptor interactor 10 (TRIP10), mRNA] and the nucleotide sequence deposited in the NCBInr database under NCBI accession number NM_053920.1 [*Rattus norvegicus* thyroid hormone receptor interactor 10 (Trip10), mRNA], as well as the nucleotide sequence of human Gene TRIP10 deposited at the UCSC website under UCSC ID uc002mfq.1, two primer pairs "hPromoter_Trip10_1" and "r_Trip_bis-3" as shown in Table 1, which were designed for the human and rat Trip10 promoters, respectively, were used in the following PCR experiments.

TABLE 1

Primer pairs for the human and rat Trip10 promoter.

| Source | Gene | Primer | Sequence (5'→3') |
|---|---|---|---|
| Human | Trip10 | hPromoter_Trip10_1_F | ctcgagcccatttgagactagccacagaac (SEQ ID NO: 1) |
| | | hPromoter_Trip10_1_R | ctcgagagataaacttcgagagagagcgga (SEQ ID NO: 2) |
| Rat | Trip10 | r_Trip10_bis-3_L | ggaagagtgggggtgggag (SEQ ID NO: 3) |
| | | r_Trip10_bis-3_R | tcccaaactattcatcctttccttca (SEQ ID NO: 4) |

The genomic DNAs of human and rat MSCs were purified using QIAamp DNA Mini Kit (Qiagen, #51304), respectively. The genomic DNA of human MSCs was used as a template in a polymerase chain reaction (PCR) experiment using the hPromoter_Trip10_1 primer pair to generate a PCR product containing the human Trip10 promoter, whereas the genomic DNA of rat MSCs was used as a template in a PCR experiment using the r_Trip_bis-3 primer pair to generate a different PCR product containing the rat Trip10 promoter. The two different PCR products with the right size were recovered by subjecting the respective PCR reaction mixtures to agarose gel electrophoresis, followed by purification using the QIAquick® Gel Extraction Kit (Qiagen, #28704)

The two different PCR products thus purified were respectively incorporated into a TA cloning vector (TOPO TA cloning kit, Invitrogen, #K450001) to form two different recombinant vectors, followed by transformation of the same into competent *E. coli* DH5α cells. Colonies growing from the transformed *E. coli* DH5α cells were screened using solid agar plates containing ampicillin. Plasmid DNAs were purified from ampicillin-resistant colonies using the QIAprep Spin Miniprep kit (Qiagen, #27104), and were enzyme restricted and sequenced for confirmation. The plasmid DNAs thus purified were used as a template in a PCR experiment using the following M13 primer pair:

```
M13_F primer
5'-gttttcccagtcacgac-3'          (SEQ ID NO: 5)

M13_R primer
5'-gccagggttttcccagtcacga-3'     (SEQ ID NO: 6)
```

This PCR experiment resulted in the formation of two different PCR products, which were purified using the QIAquick PCR purification Kit (Qiagen, cat. #28104) and used in the following experiments.

2. In Vitro DNA Methylation:

4 µgs of the two different PCR products as purified above were respectively methylated by incubation with 20 U CpG methyltransferase (M.SssI) (New England BioLabs, # M0226L) at 37° C. for 4 hours in the presence of 4 µL of 160 µM S-adenosylmethionine (SAM)(New England BioLabs, # M0226L), followed by heating at 65° C. for 5 minutes.

3. Transfection:

The two different methylated PCR products were respectively transfected into human and rat MSCs using a Fluorescent Arrest-In transfection reagent (FAI)(Open Biosystem, # ATR4167) according to the manufacturer's instructions. In brief, 20 nM of a methylated PCR product were used to transfect $5 \times 10^6$ MSCs in total. α-MEM was initially mixed with FAI at room temperature for 10 to 15 minutes. The methylated PCR product was subsequently added and the resultant mixture was allowed to stand at room temperature for 10 more minutes to form a transfection mixture. The MSCs were washed twice with PBS, followed by incubation with the transfection mixture in an incubator with culture conditions set at 37° C. and 95% $O_2$/5% $CO_2$ for 4 hours. Thereafter, MSC culture medium was added for subsequent cultivation. The MSCs were repeatedly subjected to transfection with the methylated Trip10 DNA (me_Trip10 DNA) on Day 0, 2, and 4 to form transfected MSCs. The fluorescence of FAI was used to evaluate the efficiency of transfection. Almost 100% of the transfected cells showing red fluorescence indicated the success in transfection. In addition, the MSCs were transfected with FAI alone and a combination of FAI and the non-methylated PCR product so as to form the control and mock-transfected MSCs, respectively.

4. Bisulfite Sequencing:

Two days after the third transfection, genomic DNAs were purified from the transfected human and rat MSCs using QIAamp DNA Mini Kit (Qiagen, #51304), respectively. 0.5 µg of the purified genomic DNA was bisulfite converted using the EZ DNA Methylation kit (Zymo Research, #D5001) according to the manufacturer's instructions. PCR was performed in 25 µL of a reaction mixture containing 2 µL of the bisulfite converted genomic DNA (in a total amount of 0.01 µg), 4 µL of primer pair (2.5 µM), 2.5 µL of dNTPs (10 mM), 5 µL of $MgCl_2$ (25 mM), 2.5 µL of 10× Taq buffer, 0.2 µL of Taq DNA polymerase (Fermentus, #EP0402) and 8.8 µL of dd$H_2$O. The primers used for PCR amplification are listed in Table 1. The PCR amplification was performed on a Mastercycler PCR machine (Eppendorf), starting with a 10 min denaturation at 95° C., then running for 40 cycles as follows: 94° C. held for 45 sec for denaturation; ramping down to 54° C. (0.3° C./sec); 54° C. held for 1 min for primer annealing; ramping up to 72° C. (0.3° C./sec); and 72° C. held for 1 min and 15 sec for elongation, followed by an extra extension at 72° C. for 10 min.

The amplified PCR products were run on an agarose gel, followed by purification using a QIAquick® Gel Extraction Kit (Qiagen, #28704). The purified PCR products were subcloned using the TOPO TA cloning kit, (Invitrogen, # K450001). Plasmid DNAs of 10~15 insert-positive clones were isolated by a QIAprep Spin Miniprep kit (Qiagen) and sequenced by Trigene Company (Taiwan) using the ABI sequencing system (Applied Biosystems).

5. Semi-Quantitative Methylation-Specific PCR (qMSP):

The targeted DNA methylation was validated by semi-quantitative methylation-specific PCR (qMSP). The qMSP experiment was conducted according to the procedures as described in P. S. Yan et al. (2006), *Clin. Cancer Res.*, 64:6626-6636. The bisulfite-converted genomic DNAs as obtained in the preceding section of "4. Bisulfite sequencing" were used as the template. CpGenome Universal Methylated DNA (Chemicon, #S7821) was bisulfite converted as well and used as a positive control.

The qMSP experiment was performed in 25 µL of a reaction mixture containing 2 µL of template (bisulfite converted DNA), 4 µL of primer pair (2.5 µM), 12.5 µL of 2× reaction buffer (SYBR Green Realtime PCR Master Mix, Toyobo, # QPK201) and 6.5 µL of dd$H_2$O. The primers used in the qMSP experiment are listed in Table 2, in which the primer pairs "human h_Col2A1" and "rat r_Col2A1" listed therein were respectively used to amplify the serially diluted (1/10, 1/100 and 1/1000) bisulfite-converted CpGenome Universal Methylated DNA, so as to generate standard curves for quantification and to normalize the amounts of the methylated DNAs amongst test samples.

TABLE 2

Primers used in the qMSP experiment.

| Source | Gene | NCBI Accession No. | Primer | Sequence (5'→3') |
|---|---|---|---|---|
| Human | Trip10 | NM_004240 | h_Trip10_L_M2 | gaagtttatttgggagttttagtacgt (SEQ ID NO: 7) |
| | | | h_Trip10_R_M2 | ataacctctctcaaccgcc (SEQ ID NO: 8) |
| Rat | Trip10 | NM_053920.1 | r_Trip10_L_M1 | Tttggtttttaataggggc (SEQ ID NO: 9) |
| | | | r_Trip10_R_M1 | aaaacaatatacccaacctcgc (SEQ ID NO:10) |
| Human | Col2A1 | NM_033150 | h_Col2A1_F | gggaagatgggatagaagggaatat (SEQ ID NO: 11) |

TABLE 2-continued

Primers used in the qMSP experiment.

| Source Gene | | NCBI Accession No. | Primer | Sequence (5'→3') |
|---|---|---|---|---|
| | | | h_Col2A1_R | tctaacaattataaactccaaccaccaa (SEQ ID NO: 12) |
| Rat | Col2A1 | NM_012929 | r_Col2A1_F | ggtaggtgtgggttttggttc (SEQ ID NO: 13) |
| | | | r_Col2A1_R | aactccgattatatactcccgat (SEQ ID NO: 14) |

The qMSP experiment was performed on the Bio-Rad iQ5 real time PCR machine, starting with a 7 min and 30 sec denaturation at 95° C., then running for 45 cycles as follows: 95° C. held for 30 sec and 60° C. held for 1 min. For melting curve validation, PCR was performed at the following conditions: 55° C. held for 1 min and 30 sec, and then ramping up to 95° C. (0.5° C./30 sec). The presence of a single melting peak confirmed the generation of a single PCR product.

The methylation percentage was calculated by the following equation:

$$A=(B/C) \times 100$$

A: Methylation percentage (%)
B: Intensity of amplifications by the human h_Trip10 or rat r_Trip10 primer pair
C: Intensity of amplifications by the human h_Col2A1 or rat r_Col2A1 primer pair In addition, the methylation percentage of the Trip10 promoter in the mock-transfected cells was set as 100%, and the methylation percentage of the Trip10 promoter in cells transfected with the me_Trip10 DNA was normalized by that of the mock-transfected cells.

6. Real Time Reverse Transcriptase Polymerase Chain Reaction (Real Time RT-PCR):

Two days after the third transfection, total RNAs were purified from the MSCs using RNeasy kit (Qiagen) according to the manufacturer's instructions. For first strand cDNA synthesis, 2 μg of RNA was initially mixed with 2 μL of 10× buffer and 2 μL of DNase I to make a total volume of 20 μL, and then incubated at room temperature for 15 minutes. The resultant mixture was added with 2 mL of EDTA (25 μM) and incubated at 65° C. for 5 minutes. After admixing with 2 μL of oligo-dT (10 mM) and 0.4 μL of RNase Out, the mixture was incubated at 65° C. for 5 minutes. Thereafter, the resultant mixture was added with 5 μL of 10× buffer, 2 μL of dNTPs (10 mM) and 2 μL of SuperScript reverse transcriptase (Invitrogen) and incubated at 42° C. for 90 minutes. Except it was performed in a Bio-Rad iQ5 real time PCR machine, semi-quantitative real-time PCR was then performed to quantify the gene expression under the same conditions as described in Y. W. Leu et al. (2004), Cancer Res., 64:8184-8192.

GAPDH mRNA expression was used as internal control. Real time PCR was used to determine the expression levels of Trip10 mRNA in both the mock-transfected MSCs and the MSCs transfected with the me_Trip10 DNA. The amount of Trip10 mRNA in the mock-transfected MSCs was set as 100% and the amount of Trip10 mRNA in the MSCs transfected with the me_Trip10 DNA was normalized by that of the mock-transfected MSCs.

7. Neuronal Induction of MSCs:

Two days after the third transfection, the MSCs were plated into 6 new well plates ($5 \times 10^4$ cells/well). After the cells were attached, MSC culture medium was replaced with neuronal pre-induction medium [Dulbecco's Modified Eagle's Medium (DMEM) supplemented with 20% FBS, 10 ng/mL bFGF and 1 mM β-mercaptoethanol] and kept in an incubator with culture conditions set at 37° C. and 95% $O_2$/5% $CO_2$ for 24 hours. Thereafter, the neuronal pre-induction medium was removed, and the MSCs were washed with PBS, followed by incubation with neuronal induction medium [DMEM supplemented with 100 μM BHA, 10 μM forskolin, 2% DMSO, 25 mM KCl, 2 mM valproic acid, 1× B27 supplement, 10 ng/mL bFGF and 10 ng/mL platelet-derived growth factor (PDGF)]. Culturing of the cells was continued until eight days after the third transfection. Morphological changes (such as multiple neurite-like processes) of the cells were observed by an optical microscope to prove the success of induction.

8. Immunostaining:

To further prove the success of induction, biochemical changes of rat MSCs transfected with me_Trip10 DNA versus mock-transfected rat MSCs were observed in terms of the presence of NeuN (a neuron-specific marker) and TRIP10 in rat MSCs.

Both the rat MSCs transfected with me_Trip10 DNA and the mock-transfected rat MSCs, which had been subjected to cultivation with neuronal pre-induction medium for 24 hours as described in section "7. Neuronal Induction of MSCs," as well as the mock-transfected rat MSCs which had been subjected to cultivation with neuronal induction medium for 24 hours, were washed twice with 1×PBS, followed by fixation with 2% formaldehyde in PBS at room temperature for 30 minutes. The fixed rat MSCs were washed with PBS and then permeabilized with 0.5% NP40 in PBS at room temperature for 5 minutes. Thereafter, the rat MSCs were washed with PBS and then blocked with horse serum in PBS (1:100) at room temperature for 30 minutes.

After removal of horse serum by washing with PBS, the rat MSCs were incubated with anti-NeuN antibody (Chemicon, #377) or anti-TRIP10 antibody (AbCam, # 33874) as primary antibody in 3% BSA/PBS (anti-NeuN antibody, 1:500; anti-TRIP10 antibody, 1:1000) at room temperature for 1 hour. The incubation was terminated by washing with PBS. The rat MSCs were then incubated with a secondary antibody conjugated with Texas Red (Vector Lab, TI-2020)(for anti-NeuN antibody) or a secondary antibody conjugated with fluorescencin (Vector Lab, Fl-1000)(for anti-TRIP10 antibody) in 3% BSA/PBS (1:1000) at room temperature for 1 hour, followed by washing to remove excess secondary antibody. Before mounting, 4,6-diamidino-2-phenylindole (DAPI) was added to localize the nuclei. A fluorescent microscope (Olympus) was used to observe the distribution of NeuN and TRIP10.

Results:

In the Examples of this invention, the applicants tried to find out the biological function(s) of the Trip10 gene in human and rat mesenchymal stem cells (MSCs). The applicants firstly cloned the human and rat Trip10 promoters based on three known sequences and used the same to prepare methylated Trip10 DNA (me_Trip10 DNA). Human and rat MSCs were then transfected with the me_Trip10 DNA.

Figure 1:
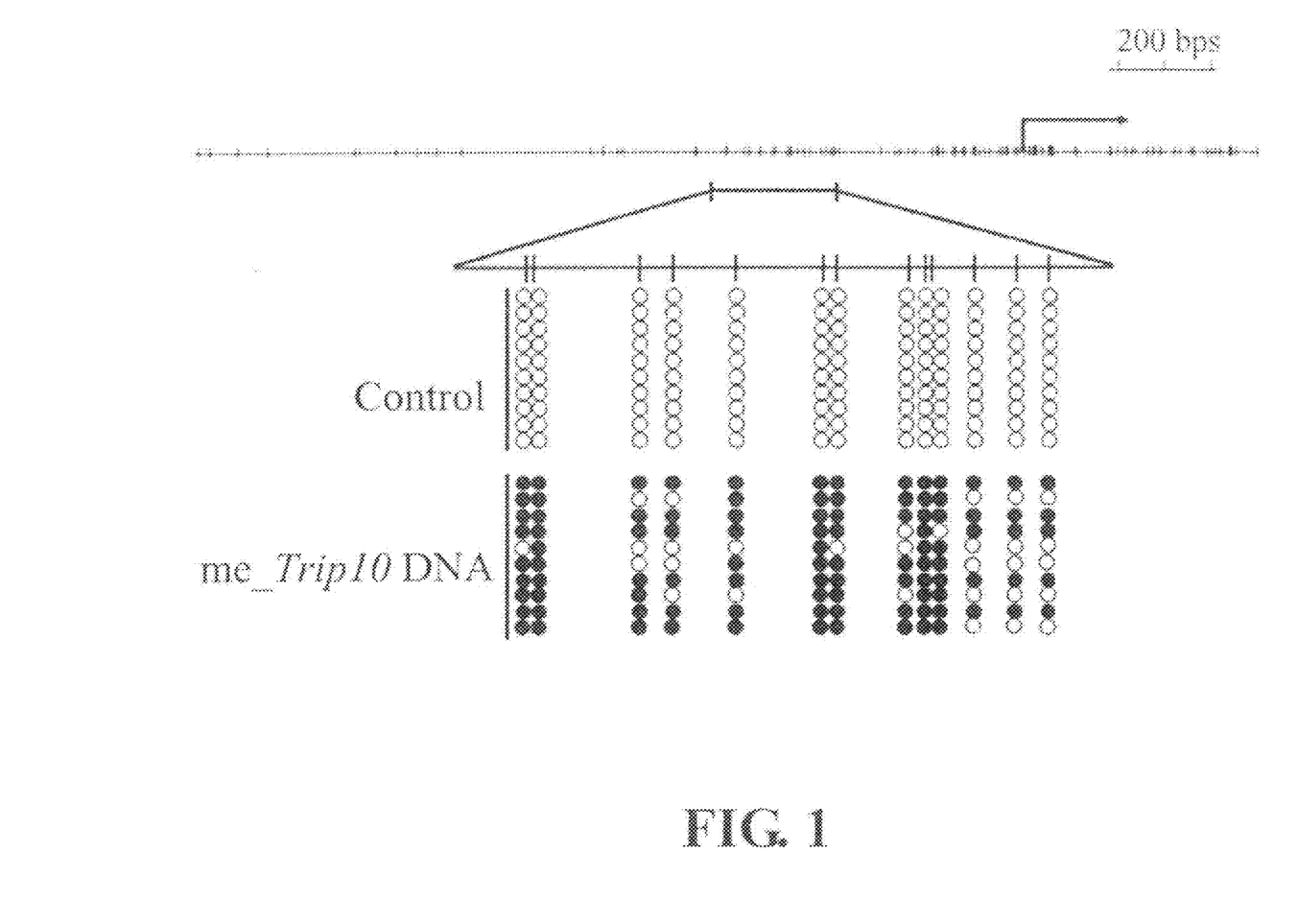
FIG. 1 shows the bisulfite sequencing results of the Trip10 promoter in human mesenchymal stem cells (MSCs) transfected with methylated Trip10 DNA (me_Trip10 DNA), in which filled and open circles indicate methylated CpG dinucleotides and non-methylated CpG dinucleotides, respectively, and the bent arrow indicates the transcriptional start site.

FIG. 1 shows the bisulfite sequencing results of the Trip10 promoter in human MSCs transfected with me_Trip10 DNA. It can be seen from FIG. 1 that in vitro transfection of methylated Trip10 DNA was able to induce endogenous DNA methylation in human MSCs. No methylation (open circles) was found in the CpG dinucleotides of the Trip10 promoter region in the control MSCs. However, these CpG dinucleotides were methylated (filled circles) in 8 out of the 10 clones obtained from human MSCs transfected with methylated Trip10 DNA. These data demonstrate that the methylated Trip10 DNA induced methylation of the Trip10 promoter in the human MSCs.

Figure 2:
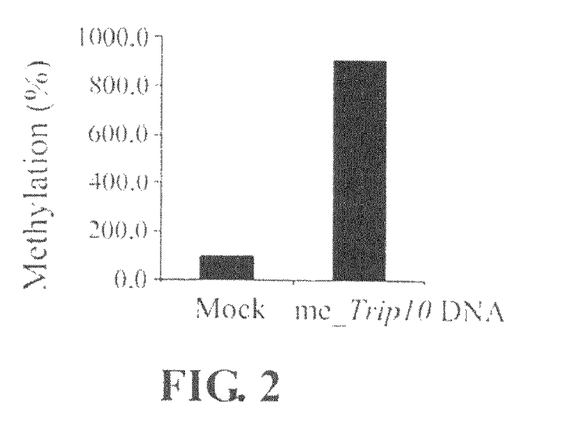
FIG. 2 shows the methylation extent of the Trip10 promoter in human MSCs transfected with me_Trip10 DNA versus the mock-transfected human MSCs as determined by semi-quantitative methylation-specific PCR (qMSP)
Figure 3:
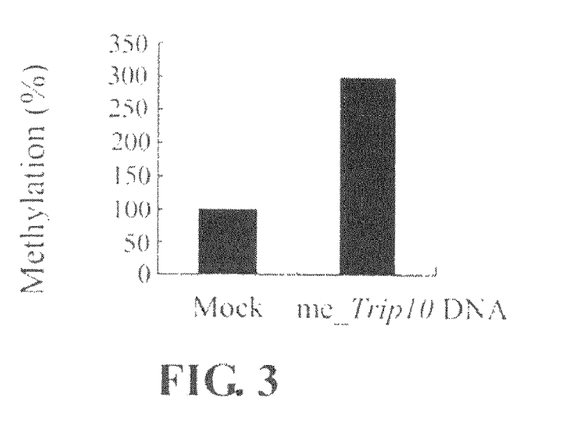
FIG. 3 shows the methylation extent of the Trip10 promoter in rat MSCs transfected with me_Trip10 DNA versus the mock-transfected rat MSCs as determined by qMSP.

The applicants further studied to which extent the methylated Trip10 DNA could induce methylation of the Trip10 promoter in human and rat MSCs by semi-quantitative methylation-specific PCR (qMSP) experiments. The obtained data reveal that endogenous methylation was substantially increased in MSCs transfected with me_Trip10 DNA as compared to mock-transfected MSCs. As can be seen from FIGS. 2 and 3, the human MSCs transfected with me_Trip10 DNA exhibit about 9-fold increase in Trip10 promoter methylation, whereas the rat MSCs transfected with me_Trip10 DNA exhibit about 3-fold increase in Trip10 promoter methylation.

Figure 4:
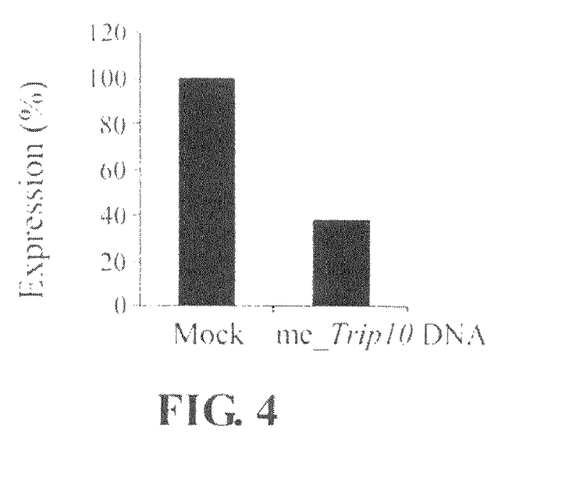
FIG. 4 shows the expression levels of Trip10 mRNA in human MSCs transfected with me_Trip10 DNA versus the mock-transfected human MSCs as determined by real time reverse transcriptase PCR.

The influence of the methylated Trip10 DNA upon the expression of the Trip10 gene was also studied by real time reverse transcriptase PCR. It can be seen from FIG. 4 that the expression level of Trip10 mRNA in human MSCs transfected with me_Trip10 DNA was decreased by about 60%, as compared to mock-transfected MSCs.

The applicants explored the biological function(s) of the Trip10 gene by comparing the morphological difference(s) between MSCs transfected with the me_Trip10 DNA and mock-transfected MSCs.

Figure 5:
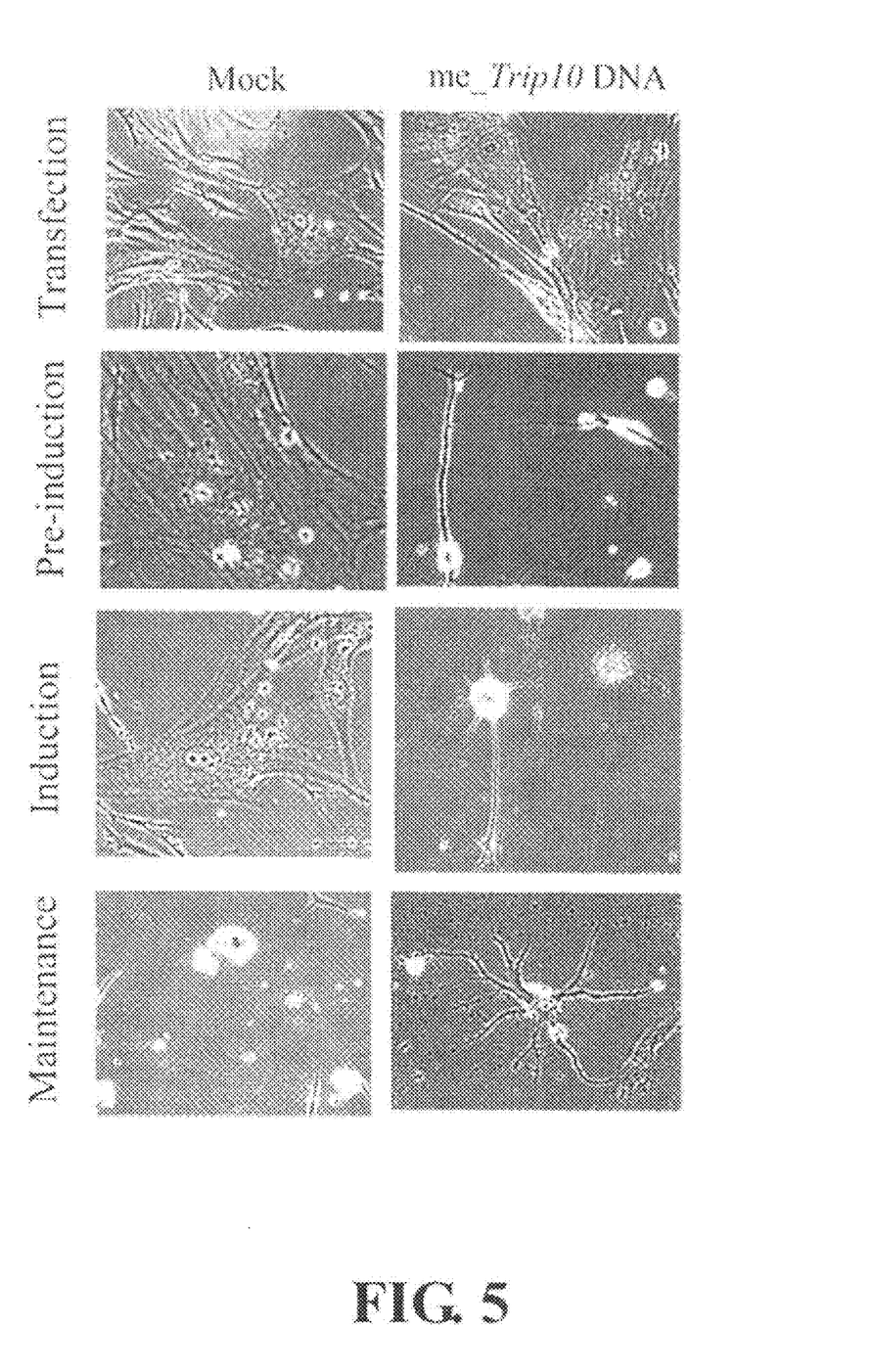
FIG. 5 shows the morphological changes of human MSCs transfected with me_Trip10 DNA versus mock-transfected human MSCs during four different culture stages (transfection, pre-induction, induction, and maintenance)
Figure 6:
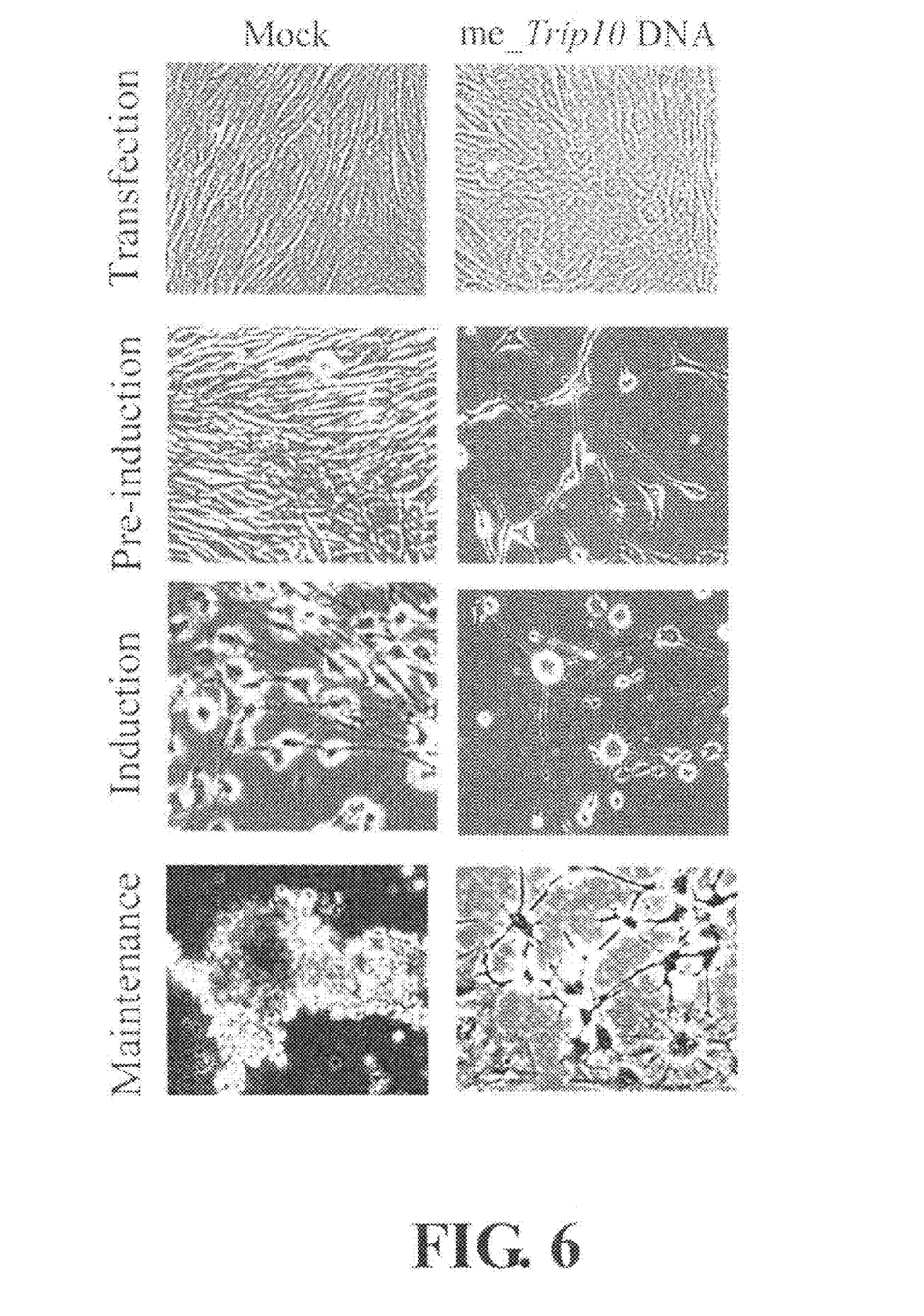
FIG. 6 shows the morphological changes of rat MSCs transfected with me_Trip10 DNA versus mock-transfected rat MSCs during four different culture stages (transfection, pre-induction, induction, and maintenance)

FIGS. 5 and 6 respectively show the morphological changes of human and rat MSCs transfected with me_Trip10 DNA versus mock-transfected MSCs during four different culture stages (transfection, 2 days after the third transfection; pre-induction, 1-day cultivation with neuronal pre-induction medium; induction, 1-day cultivation with neuronal induction medium; and maintenance, 8 days after the third transfection).

Referring to FIG. 5, transfection with me_Trip10 DNA does not cause apparent morphological changes of the human MSCs. However, human MSCs transfected with me_Trip10 DNA developed neuron-like phenotype after 1-day pre-induction treatment, whereas the mock-transfected human MSCs retained their original MSC morphology. Both the human MSCs transfected with me_Trip10 DNA and the mock-transfected human MSCs exhibit neuron-like structure after 1-day neuronal induction. The majority of the mock-transfected cells died at the maintenance stage, whereas many of human MSCs transfected with me_Trip10 DNA survived at the maintenance stage. As shown in FIG. 6, similar results are also observed for rat MSCs.

The results of FIGS. 5 and 6 reveal that methylation of the Trip10 promoter accelerates MSC-to-neuron differentiation and prevents the differentiated neurons from cell death, suggesting that TRIP10 might be involved in the maintenance of the pluripotency of human or rat MSCs and the survival of the human or rat MSC-derived neuronal cells.

The influence of transfection with methylated Trip10 DNA upon rat MSCs was further studied by evaluating the NeuN distribution and the TRIP10 distribution in rat MSCs.

Figure 7:
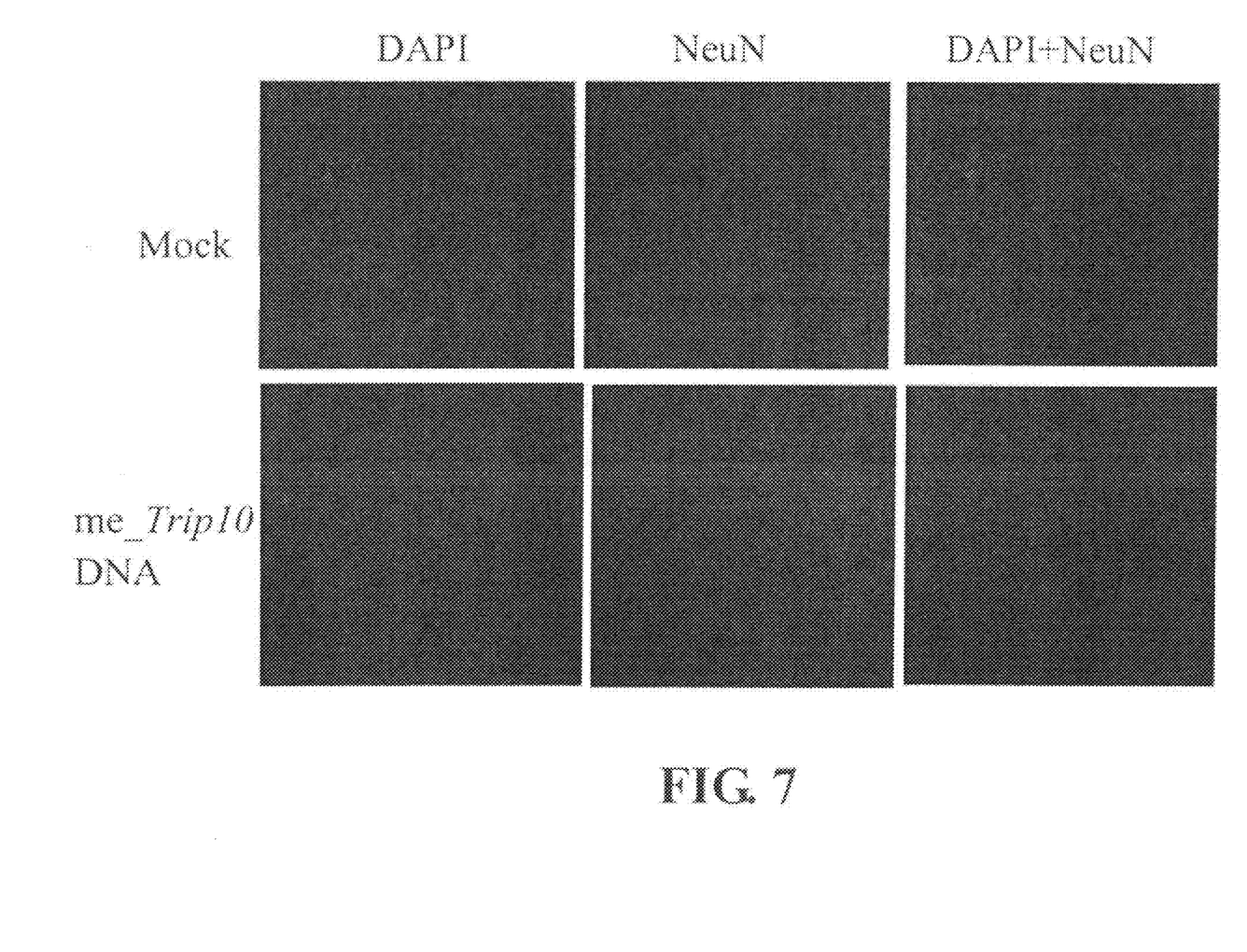
FIG. 7 shows the NeuN distribution in rat MSCs transfected with me_Trip10 DNA versus the mock-transfected rat MSCs after cultivation with neuronal pre-induction medium for 24 hours, in which the nuclei (blue colored) of the cells were localized by staining with 4,6-diamidino-2-phenylindole (DAPI), and the presence of NeuN (a neuron-specific marker) in the cells was observed by incubating the cells with an anti-NeuN antibody (Chemicon, #377), followed by incubation with a secondary antibody conjugated with Texas Red (Vector Lab, #TI-2020)

FIG. 7 shows the NeuN distribution in rat MSCs transfected with me_Trip10 DNA versus mock-transfected rat MSCs after cultivation with neuronal pre-induction medium for 24 hours. It can be seen from FIG. 7 that transfection of me_Trip10 DNA accelerated rat MSC-to-neuron differentiation in rat MSCs transfected with me_Trip10 DNA. The immunostaining results reveal that the pre-induction treatment does not change the stem cell property in the mock-transfected rat MSCs, as evidenced by lack of immunoreactivity with NeuN. However, NeuN was readily detected in rat MSCs transfected with me_Trip10 DNA, indicating that the decrease in the expression of endogenous TRIP10 accelerates neuronal differentiation.

Figure 8:
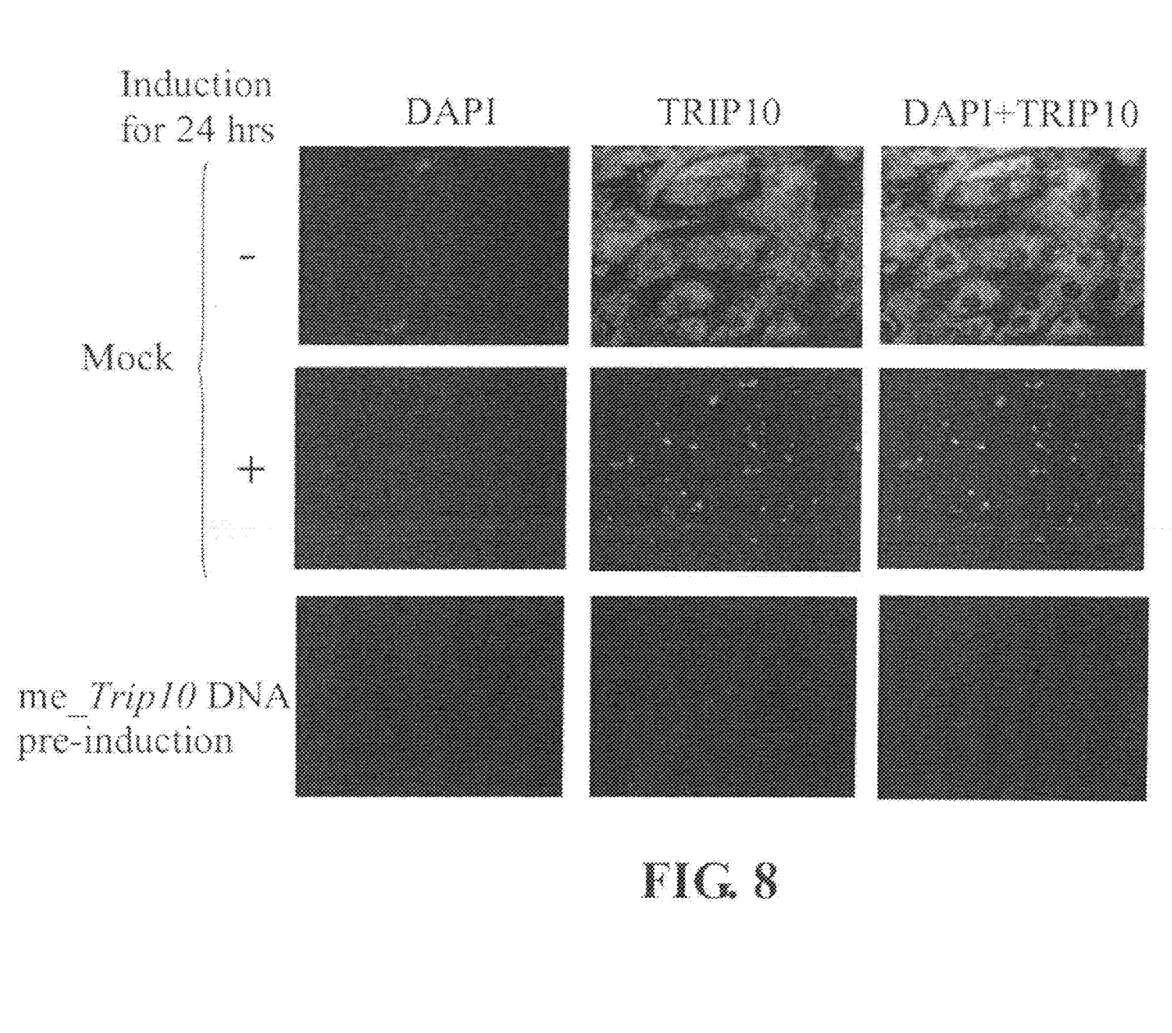

FIG. 8 shows the TRIP10 distribution in rat MSCs transfected with me_Trip10 DNA versus mock-transfected rat MSCs with or without cultivation with neuronal induction medium for 24 hours. It can be seen from FIG. 8 that methylation of the Trip10 promoter alone is sufficient to accelerate the cell fate change in rat MSCs transfected with me_Trip10 DNA. Before neuronal induction treatment, TRIP10 was widely distributed in the cytoplasm of the mock-transfected rat MSCs (see the top panels). After neuronal induction treatment, no TRIP10 was found in cytoplasm, and the remaining TRIP10 was re-directed to the peri-nuclei region (see the middle panels). However, in rat MSCs transfected with me_Trip10 DNA, the neuronal pre-induction treatment was sufficient to trigger the change in TRIP10 distribution (see the bottom panels) similar to that of the mock-transfected cells after neuronal induction. The immunostaining patterns prove the success of TRIP10 knock down in rat MSCs transfected with me_Trip10 DNA and reveal that methylation of the Trip10 promoter alone was sufficient to accelerate the cell fate change.

In conclusion, the applicants developed a method to determine the biological function(s) of a target gene in a cell. The above results reveal that methylation of the Trip10 promoter accelerates human and rat MSC-to-neuron differentiation and keeps the differentiated neurons from cell death, indicating that the method of this invention is not only sufficient to elevate DNA methylation within a target gene but also changes the cell fate. Practically, the staged MSC-to-neuron differentiation and the escape from cell death for the differentiated neurons further make stem cells easier to use and easier in control.

All patents and literature references cited in the present specification as well as the references described therein, are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

We claim:

1. A method to determine which biological function a target gene in a cell is associated with, the target gene having a nucleotide sequence including a promoter and a first exon region, the method comprising:
   separately culturing a first population and a second population of the cell under same culturing conditions, the first population of the cell differing from the second population of the cell in that the first population of the cell has accepted the introduction of a methylated polynucleotide selected from the group consisting of:
   (i) a single-stranded molecule, which has a nucleotide sequence identical to or fully complementary to that of a portion of the target gene's nucleotide sequence at the promoter and/or the first exon region thereof;
   (ii) a double-stranded molecule, one strand of which has a nucleotide sequence identical to or fully complementary to that of a portion of the target gene's nucleotide sequence at the promoter and/or the first exon region thereof; and
   (iii) a combination of (i) and (ii);
   comparing the first population and the second population of the cell to determine which biological difference is present there between; and
   determining which biological function the target gene is associated with based on the biological difference present between the first population and the second population of the cell
   wherein the cell is a mesenchymal stem cell; and wherein introduction of the methylated polynucleotide into the first population of the cell does not cause death of the first population of the cell in the culturing step,
   wherein the target gene is a TRIP10 gene.

2. The method as claimed in claim 1, wherein the methylated polynucleotide is a double-stranded molecule, one strand of which has a nucleotide sequence identical to that of a portion of the target gene's nucleotide sequence at the promoter thereof.

3. The method as claimed in claim 1, wherein the methylated polynucleotide is a single-stranded molecule, which has a nucleotide sequence identical to that of a portion of the target gene's nucleotide sequence at the promoter thereof.

4. The method as claimed in claim 1, wherein the methylated polynucleotide has at least one methylated cytosine nucleotide.

5. The method as claimed in claim 1, wherein the methylated polynucleotide has a length ranging from 22 to 2000 nucleotides.

6. The method as claimed in claim 1, wherein the biological difference is selected from the group consisting of a biochemical difference, a physiological difference, a morphological difference, and combinations thereof.

7. The method as claimed in claim 1, wherein the methylated polynucleotide is introduced into the first population of the cell via an approach selected from the group consisting of: gene gun, electroporation, microinjection, heat shock, calcium phosphate precipitation, magnetofection, nucleofection, lipofection, use of a transfection reagent, use of a cationic polymer, and combinations thereof.

* * * * *

SEQUENCE LISTING

<160> NUMBER OF SEQ ID NOS: 14

<210> SEQ ID NO 1
<211> LENGTH: 30
<212> TYPE: DNA
<213> ORGANISM: Artificial
<220> FEATURE:
<223> OTHER INFORMATION: Forward primer hPromoter_Trip10_1_F for PCR of
      human Trip10 gene

<400> SEQUENCE: 1
ctcgagccca tttgagacta gccacagaac                                    30

<210> SEQ ID NO 2
<211> LENGTH: 30
<212> TYPE: DNA
<213> ORGANISM: Artificial
<220> FEATURE:
<223> OTHER INFORMATION: Reverse primer hPromoter_Trip10_1_R for PCR of
      human Trip10 gene

<400> SEQUENCE: 2
ctcgagagat aaacttcgag agagagcgga                                    30

<210> SEQ ID NO 3
<211> LENGTH: 19
<212> TYPE: DNA
<213> ORGANISM: Artificial
<220> FEATURE:
<223> OTHER INFORMATION: Forward primer r_Trip10_bis-3_L for PCR of rat
      Trip10 gene

<400> SEQUENCE: 3
ggaagagtgg gggtgggag                                                19

<210> SEQ ID NO 4
<211> LENGTH: 26
<212> TYPE: DNA
<213> ORGANISM: Artificial
<220> FEATURE:
<223> OTHER INFORMATION: Reverse primer r_Trip10_bis-3_R for PCR of rat
      Trip10 gene

<400> SEQUENCE: 4
tcccaaacta ttcatccttt ccttca                                        26

<210> SEQ ID NO 5
<211> LENGTH: 17
<212> TYPE: DNA
<213> ORGANISM: Artificial
<220> FEATURE:
<223> OTHER INFORMATION: Forward primer M13_F for PCR

<400> SEQUENCE: 5
gttttcccag tcacgac                                                  17

<210> SEQ ID NO 6
<211> LENGTH: 22
<212> TYPE: DNA
<213> ORGANISM: Artificial
<220> FEATURE:
<223> OTHER INFORMATION: Reverse primer M13_R for PCR

<400> SEQUENCE: 6
gccagggttt tcccagtcac ga                                            22

-continued

```
<210> SEQ ID NO 7
<211> LENGTH: 27
<212> TYPE: DNA
<213> ORGANISM: Artificial
<220> FEATURE:
<223> OTHER INFORMATION: Forward primer h_Trip10_L_M2 for qMSP of human
      Trip10 gene

<400> SEQUENCE: 7
gaagtttatt tgggagtttt agtacgt                                            27

<210> SEQ ID NO 8
<211> LENGTH: 20
<212> TYPE: DNA
<213> ORGANISM: Artificial
<220> FEATURE:
<223> OTHER INFORMATION: Reverse primer h_Trip10_R_M2 for qMSP of human
      Trip10 gene

<400> SEQUENCE: 8
aataacctct ctcaaccgcc                                                    20

<210> SEQ ID NO 9
<211> LENGTH: 21
<212> TYPE: DNA
<213> ORGANISM: Artificial
<220> FEATURE:
<223> OTHER INFORMATION: Forward primer r_Trip10_L_M1 for qMSP of rat
      Trip10 gene

<400> SEQUENCE: 9
tttggttttt taataggggg c                                                  21

<210> SEQ ID NO 10
<211> LENGTH: 22
<212> TYPE: DNA
<213> ORGANISM: Artificial
<220> FEATURE:
<223> OTHER INFORMATION: Reverse primer r_Trip10_R_M1 for qMSP of rat
      Trip10 gene

<400> SEQUENCE: 10
aaaacaatat acccaacctc gc                                                 22

<210> SEQ ID NO 11
<211> LENGTH: 25
<212> TYPE: DNA
<213> ORGANISM: Artificial
<220> FEATURE:
<223> OTHER INFORMATION: Forward primer h_Col2A1_F for qMSP of human
      Col2A1 gene

<400> SEQUENCE: 11
gggaagatgg gatagaaggg aatat                                              25

<210> SEQ ID NO 12
<211> LENGTH: 28
<212> TYPE: DNA
<213> ORGANISM: Artificial
<220> FEATURE:
<223> OTHER INFORMATION: Reverse primer h_Col2A1_R for qMSP of human
      Col2A1 gene

<400> SEQUENCE: 12
tctaacaatt ataaactcca accaccaa                                           28

<210> SEQ ID NO 13
```

```
<211> LENGTH: 21
<212> TYPE: DNA
<213> ORGANISM: Artificial
<220> FEATURE:
<223> OTHER INFORMATION: Forward primer r_Col2A1_F for qMSP of rat
      Col2A1 gene

<400> SEQUENCE: 13
ggtaggtgtg ggttttggtt c                                              21

<210> SEQ ID NO 14
<211> LENGTH: 23
<212> TYPE: DNA
<213> ORGANISM: Artificial
<220> FEATURE:
<223> OTHER INFORMATION: Reverse primer r_Col2A1_R for qMSP of rat
      Col2A1 gene

<400> SEQUENCE: 14
aactccgatt atatactccc gat                                            23
```